(12) United States Patent
Halbert et al.

(10) Patent No.: US 9,272,087 B2
(45) Date of Patent: Mar. 1, 2016

(54) FLUID LINE OCCLUSION DETECTION SYSTEM AND METHODS

(71) Applicant: CareFusion 303, Inc., San Diego, CA (US)

(72) Inventors: Donald Halbert, San Diego, CA (US); Jesse Guerra, San Diego, CA (US); Stephen Bollish, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 204 days.

(21) Appl. No.: 13/928,181

(22) Filed: Jun. 26, 2013

(65) Prior Publication Data

US 2015/0005732 A1    Jan. 1, 2015

(51) Int. Cl.
*A61M 1/00* (2006.01)
*A61M 5/142* (2006.01)
*A61M 5/168* (2006.01)

(52) U.S. Cl.
CPC ....... *A61M 5/14212* (2013.01); *A61M 5/14228* (2013.01); *A61M 5/16827* (2013.01); *A61M 2005/16863* (2013.01); *A61M 2005/16868* (2013.01)

(58) Field of Classification Search
CPC .............. A61M 2005/16872; A61M 5/16859; A61M 5/172; A61M 2005/16868; A61M 2005/16863; A61M 5/16854
See application file for complete search history.

(56) References Cited

U.S. PATENT DOCUMENTS 5,695,473 A * 12/1997 Olsen ........................... 604/153

* cited by examiner

*Primary Examiner* — Rebecca E Eisenberg
(74) *Attorney, Agent, or Firm* — Fred C. Hernandez; Mintz Levin Cohn Ferris Glovsky and Popeo, P.C.

(57) ABSTRACT

The systems, methods and articles described herein are directed to at least one pressure sensor along a downstream fluid line which senses fluid pressure and assists an occlusion detection feature in determining the presence of occlusions in the downstream fluid line. In addition, the system can dynamically adapt the occlusion detection feature based on a delivery of fluid, such as a bolus, in order to prevent the system from creating a false alarm regarding an occlusion of the downstream fluid line.

7 Claims, 4 Drawing Sheets

FLUID LINE OCCLUSION DETECTION SYSTEM AND METHODS

BACKGROUND

A hospital patient often has the need for multiple intravenous (IV) infusions from multiple supplies of fluids, such as drugs. This can require the use of multiple infusion pumps that are connected to the patient and to fluid containers via fluid lines. In addition, each fluid infusion pump can be programmed to pump fluid to the patient at a variety of infusion rates. The infusion rates can depend on a number of factors including type of fluid, such as drugs, and the needs of the patient.

Infusion pumps can provide an efficient way to deliver a fluid to a patient at a programmed infusion rate, as well as deliver one or more boluses of fluid. In addition, infusion pumps can include a variety of safety features which can monitor and ensure that the proper amount of fluid is being delivered to the patient, such as at the programmed infusion rate. For example, infusion pumps can include one or more features and programs which detect for occlusions in the fluid line. Therefore, when an occlusion forms in the fluid line, such as due to a clot forming in the fluid line, an alarm can be activated which can allow a medical professional to assist in fixing the problem. This can improve patient care by ensuring the patient is receiving the prescribed or programmed amount of one or more fluids.

Although some infusion pumps include features which detect for the proper delivery of fluid, such as an occlusion detection feature, other characteristics of a delivery system can create false alarms. For example, changes in fluid infusion rates, such as during the delivery of a bolus, can cause a spike in fluid pressure which can be interpreted as an occlusion from the occlusion detection feature. These false alarms can interrupt medical staff from performing jobs, such as for caring for other patients in need. Therefore, false alarms can at least waste time and reduce the quality of care which medical staff can provide to patients.

SUMMARY

Disclosed is a patient care system for infusing fluid to a patient. The system includes at least one fluid infusion pump which is connected to a respective fluid supply for pumping the contents of a fluid supply to a patient via a fluid supply line. The system can include at least one pressure sensor positioned downstream the fluid infusion pump which can sense pressure along at least the downstream fluid line which extends between the fluid infusion pump and the patient. In addition, the system can include a programming module which can dynamically adapt, based on a programmed bolus delivery of fluid, in order to prevent the system from creating a false alarm regarding an occlusion in the downstream fluid line.

In one aspect, there is disclosed a method for dynamically adapting a fluid delivery system, the method comprising: dynamically adapting, based on a programmed bolus of fluid for delivery to a patient, an occlusion detection feature which activates an alarm when detecting at least a fluid line pressure indicating an occlusion in a fluid line; delivering the programmed bolus of fluid to the patient; and restoring the occlusion detection feature wherein the fluid line pressure indicating an occlusion in the fluid line is restored at a rate which prevents falsely activating the alarm.

In another aspect, there is disclosed a patient care system for infusing a medical fluid, the patient care system comprising: a fluid supply adapted to hold a medical fluid; a fluid line providing fluid communication between the fluid supply and a patient; an infusion pump controlling fluid flow along the fluid line between the fluid container and the patient; a pressure sensor configured to sense pressure in the fluid line between the infusion pump and the patient; and a programming module including an occlusion detection program and one or more algorithms configured to dynamically adapt, based on a programmed bolus of fluid for delivery to a patient, in order to detect occlusions in the fluid line and prevent activation of a false occlusion alarm.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

Disclosed is a patient care system for infusing fluid to a patient. The system includes at least one fluid infusion pump which is connected to a respective fluid supply for pumping the contents of a fluid supply to a patient via a fluid supply line. The system can include at least one pressure sensor positioned downstream the fluid infusion pump which can sense pressure along at least the downstream fluid line which extends between the fluid infusion pump and the patient. In addition, the system can include a programming module which can dynamically adapt, based on a programmed bolus delivery of fluid, in order to prevent the system from creating a false alarm regarding an occlusion in the downstream fluid line.

Figure 1:
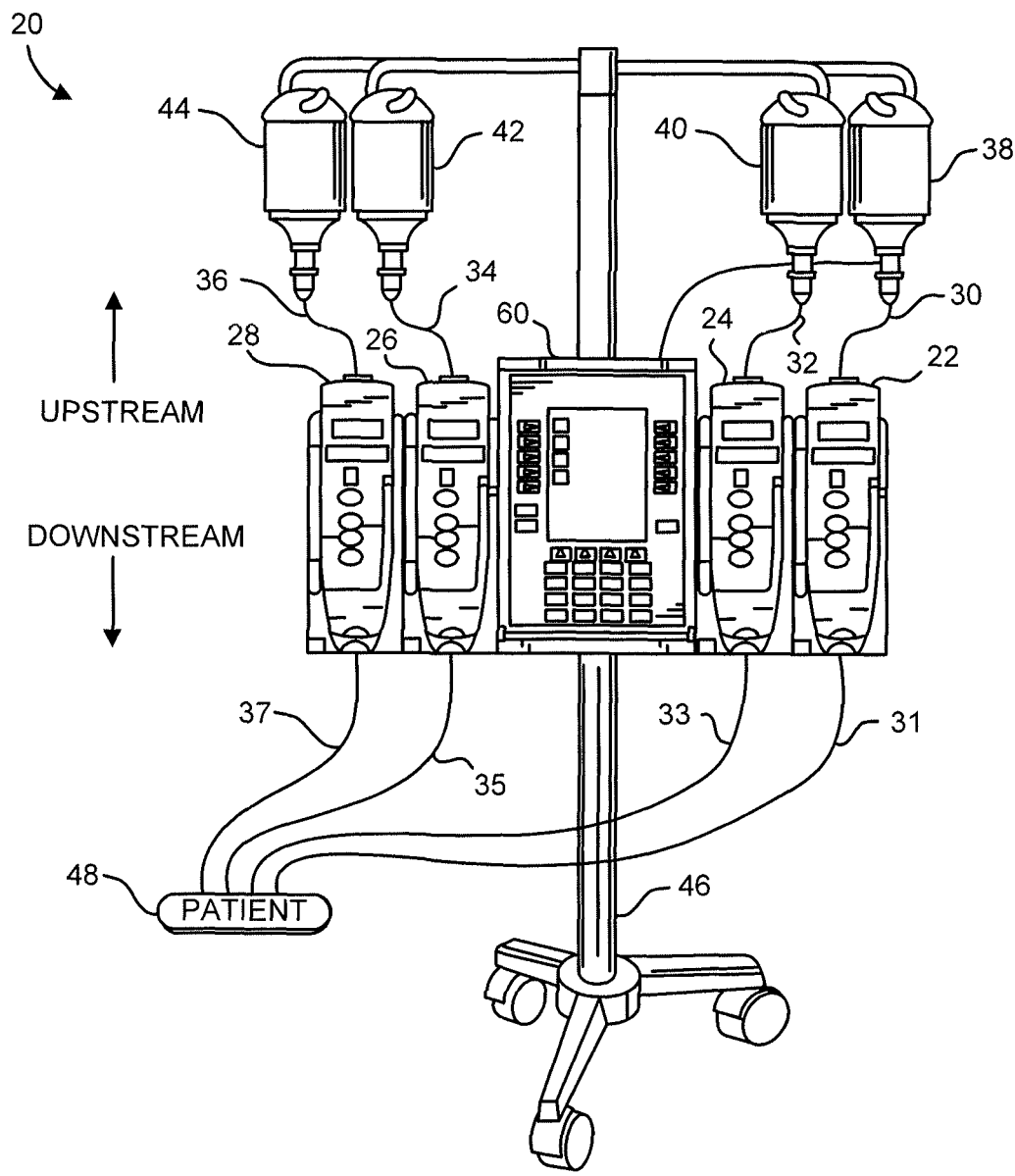
FIG. 1 is a front view of a patient care system having four fluid infusion pumps, each of which is connected to a respective fluid supply for pumping the contents of the fluid supply to a patient.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as tubing, through which fluid can flow through.

Fluid supplies 38, 40, 42, and 44, which may take various forms but in this case are shown as bottles, are inverted and suspended above the infusion pumps 22, 24, 26 and 28. Fluid supplies may also take the form of bags or other types of containers. Both the patient care system 20 and the fluid supplies 38, 40, 42, and 44 are mounted to a roller stand or IV pole 46.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 1. Many have check valves, drip chambers, valved ports, connectors, and other devices well known to those skilled in the art. These other devices have not been included in the drawings so as to preserve clarity of illustration. In addition, it should be noted that the drawing of FIG. 1 is not to scale and that distances have been compressed for the purpose of clarity. In an actual setting, the distance between the bottles 38, 40, 42, and 44 and the infusion pump modules 22, 24, 26, and 28 could be much greater.

Figure 2:
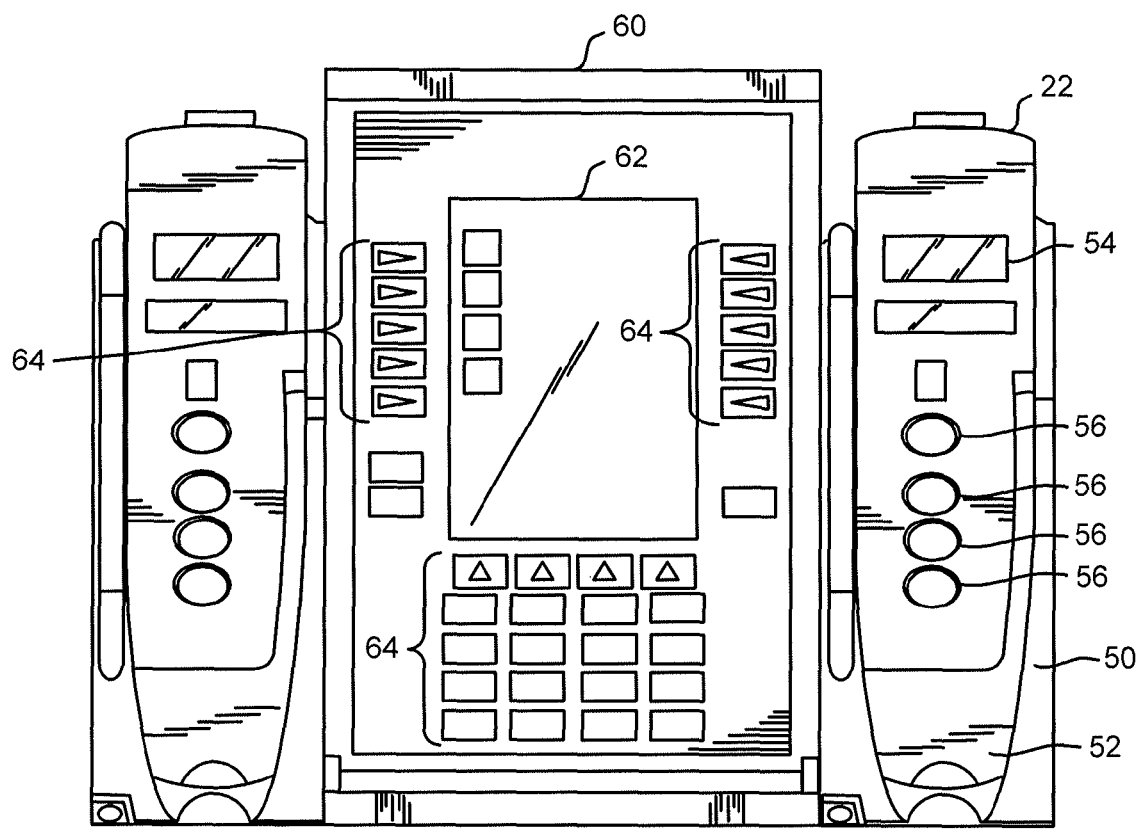
FIG. 2 is an enlarged view of a portion of the patient care system of FIG. 1 showing two of the fluid infusion pumps mounted at either side of a programming module, and the displays and control keys of each, with the programming module being capable of programming both infusion pumps.

Referring now to FIG. 2, an enlarged view of the front of the infusion pump 24 is shown. The pump includes a front door 50 and a handle 52 that operates to lock the door in a closed position for operation and to unlock and open the door for access to the internal pumping and sensing mechanisms and to load administration sets for the pump. When the door is open, the tube can be connected with the pump. When the door is closed, the tube can be brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). Control keys 56 exist for programming and controlling operations of the infusion pump as desired, including programming a bolus delivery of fluid. The infusion pump 22 can also include an alarm 120, such as an audio alarm in the form of a speaker, as shown for example in FIG. 4.

In the embodiment shown, a programming module 60 is attached to the left side of the infusion pump 22. Other devices or modules, including another infusion pump, may be attached to the right side of the infusion pump 22, as shown in FIG. 1. In such a system, each attached pump represents a pump channel of the overall patient care system 20. In one embodiment, the programming module 60 is used to provide an interface between the infusion pump 22 and external devices as well as to provide most of the operator interface for the infusion pump 22.

In addition, the programming module 60 can assist in programming an infusion rate of the infusion pump 22, including programming a delivery of one or more boluses of fluid. The programming module 60 can assist in monitoring any part of the patient care system 20, including the one or more pressure sensors, in order to ensure the patient care system 20 is providing effective care to the patient. Furthermore, the programming module 60 can assist in ensuring that the proper amounts of one or more fluids are being delivered to the patient at the programmed infusion rates. Additionally, the programming module can include one or more programs which can assist in monitoring one or more fluid lines, such as to detect for occlusions in the fluid lines.

The programming module 60 can include a display 62 for visually communicating various information, such as operating parameters, alert indications, and alarm messages, including warnings or alarms. The programming module 60 may also include a speaker to provide audible alarms. The programming module can also have various input devices, including control keys 64 and a bar code scanner (not shown) for scanning information relating to the infusion, the patient, the care giver, or other. The programming module also has a communications system (not shown) with which it may communicate with external equipment such as a medical facility server or other computer and with a portable processor, such as a handheld portable digital assistant ("PDA"), or a laptop-type of computer, or other information device that a care giver may have to transfer information as well as to download drug libraries to a programming module or pump. In addition, the programming module 60 can communicate with some external equipment which can provide sensed system parameters, such as fluid line pressure and changes in infusion rate.

The communications system may take the form of a radio frequency ("RF") (radio frequency) system, an optical system such as infrared, a Blue Tooth system, or other wired or wireless system. The bar code scanner and communications system may alternatively be included integrally with the infusion pump 22, such as in cases where a programming module is not used, or in addition to one with the programming module. Further, information input devices need not be hard-wired to medical instruments, information may be transferred through a wireless connection as well.

FIG. 2 includes a second pump module 26 connected to the programming module 60. As shown in FIG. 1, more pump modules may be connected. Additionally, other types of modules may be connected to the pump modules or to the programming module 60.

Figure 3:
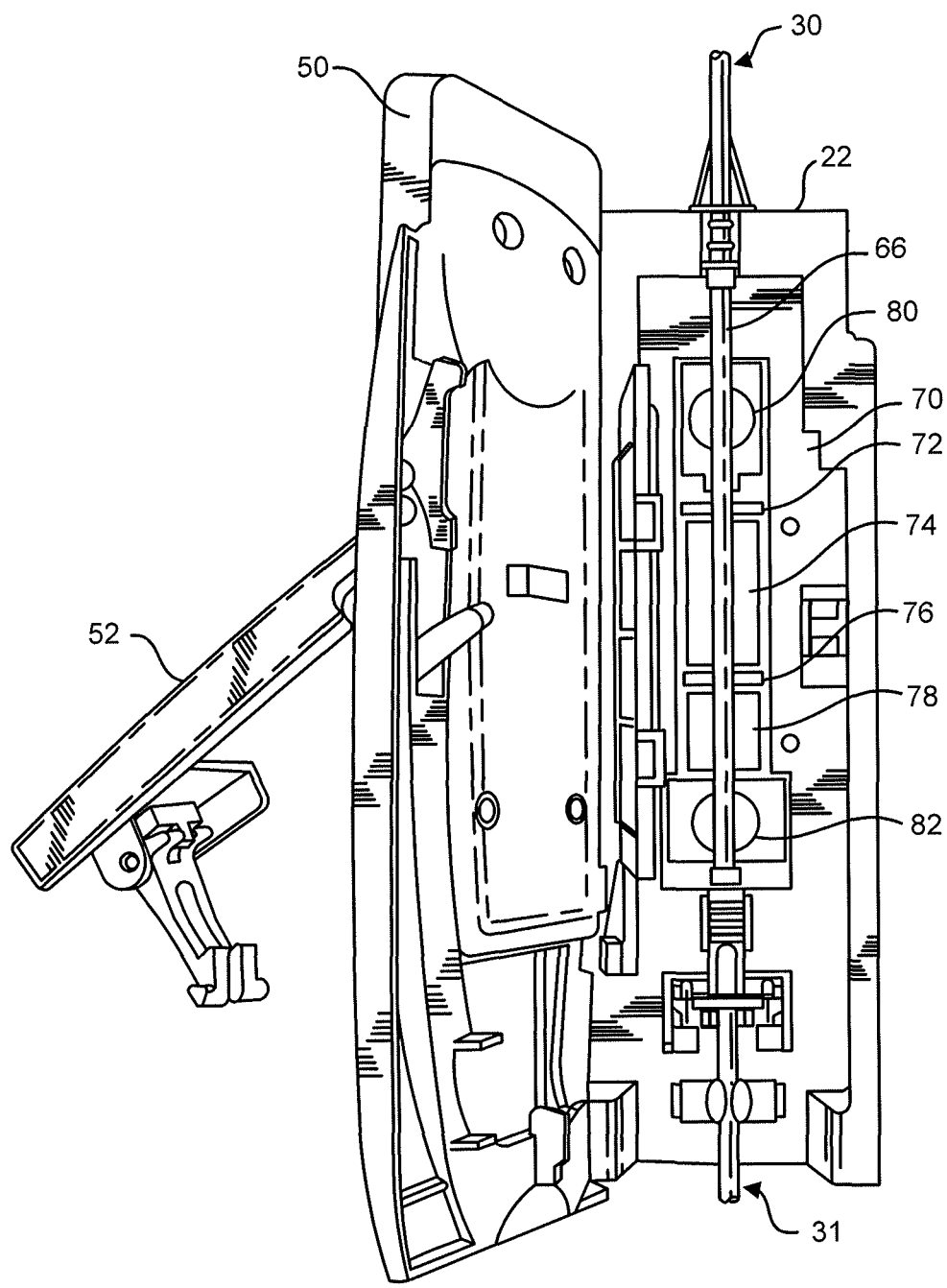
FIG. 3 is a perspective view of one of the fluid infusion pumps of FIGS. 1 and 2 with its front door open.

Turning now to FIG. 3, an infusion pump 22 is shown in perspective view with the front door 50 open, showing the upstream fluid line 30 and downstream fluid line 31 in operative engagement with the pump 22. The infusion pump 22 directly acts on a tube 66 that connects the upstream fluid line 30 to the downstream fluid line 31 to form a continuous fluid conduit, extending from the respective fluid supply 38 to the patient 48 (see FIG. 1), through which fluid is acted upon by the pump to move fluid downstream to the patient. Specifically, a pumping mechanism 70 acts as the flow control device of the pump to move fluid though the conduit.

Figure 4:
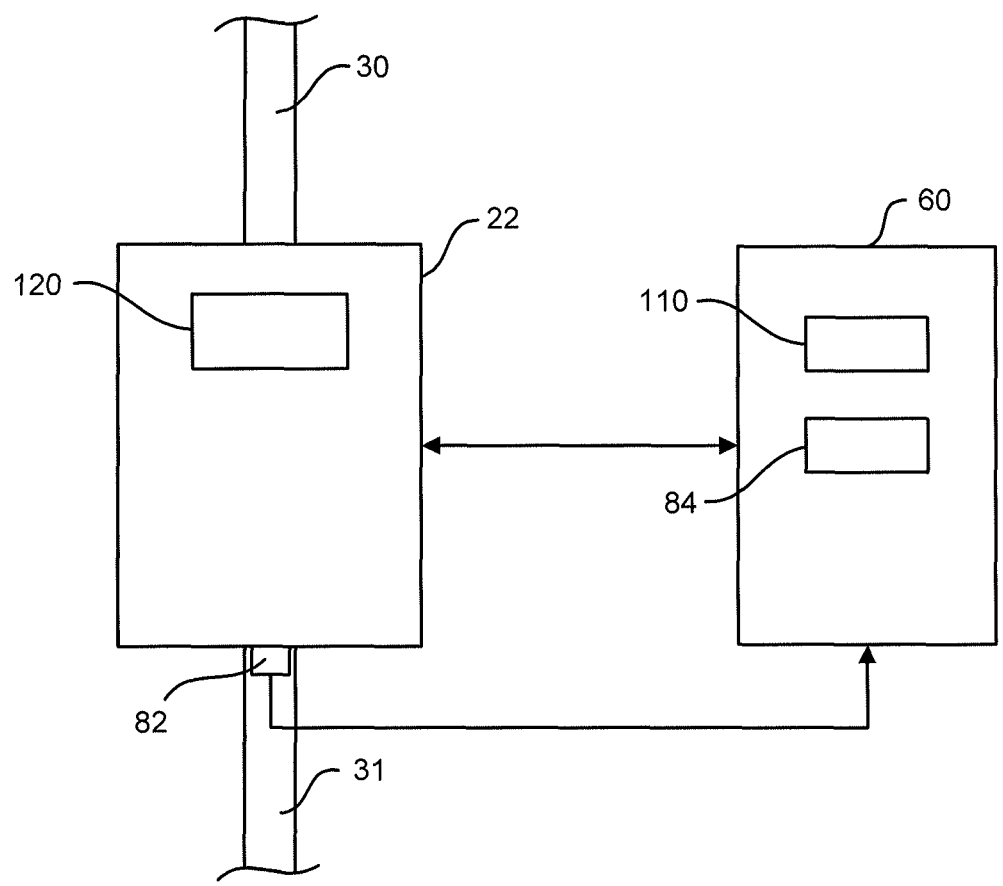
FIG. 4 is a block diagram showing an occlusion detection program of the programming module monitoring the downstream fluid line pressure of the patient care system.

As shown in FIG. 4 the programming module 60 can include an occlusion detection program 110 which is configured to assist in monitoring at least the downstream fluid line 31 and detect occlusions. The occlusion detection program 110 can detect an occlusion, such as in the downstream fluid line 31, and activate an occlusion warning. The warning can be broadcast, such as by the alarm 120, in order to allow a medical professional to assist in repairing the occluded fluid line.

In some variations, the occlusion detection program 110 can be programmed to act pursuant to one or more algorithms for assisting in detecting occlusions in the fluid line. In addition, the programming module 60 can process the occlusion detection program 110 and the one or more algorithms, such as with the processor 84, in order to determine whether there is an occlusion, such as in the downstream fluid line 31. Additionally, the occlusion detection program 110 can input a variety of information about the system, including, for example, fluid pressure sensed by the downstream pressure sensor 82. The processor 84 can then process the pressure readings input into either the occlusion detection program 110 or algorithms in order to assist in determining whether there is an occlusion in the downstream fluid line 31.

Any number of alarms can be activated upon the detection of an occlusion which can allow a medical professional to assist in relieving the fluid line of the occlusion. An occlusion can disrupt the amount of fluid programmed to be delivered to the patient which can thereby impair patient care and wellbeing. Therefore, the occlusion detection program 110 can assist in at least improving patient care.

In some variations, the occlusion detection program 110 can monitor the pressure readings from the downstream pressure sensor 82, however, the occlusion detection program 110 can monitor any number of fluid lines, including an upstream fluid line 30, such as for detecting blood clot formations or a pinched fluid line. For example, when the pressure in the downstream fluid line 31 changes, such as significantly increases, this can cause the occlusion detection program 110 to detect an occlusion.

The occlusion detection program 110 can provide several benefits for the system, including ensuring that the patient receives at least one fluid at a programmed infusion rate. Without such a detection system, the patient can be harmed by not receiving the diagnosed amount of fluid at a programmed infusion rate.

Although features such as the occlusion detection program 110 can provide several benefits, false alarms created by at least some occlusion detection features can create a variety of problems. For example, a false occlusion detection alarm can result in at least one medical professional to attend to the alarm which can take away the medical professional's time and attention away from other important patient issues.

A variety of system characteristics can cause a false alarm by at least some occlusion detection features. For example, when a bolus of fluid is delivered there can be a significant increase in pressure in the fluid line, such as in the downstream fluid line 31. The downstream pressure sensor 82 can detect the increase in pressure which can be detected by the occlusion detection feature. In addition, the occlusion detection feature can activate an alarm based on this sensed increase in pressure.

In some implementations of the system, at least one of the programming module 60 and occlusion detection program 110 can dynamically adapt to a bolus being delivered from the infusion pump 22, including automatically upon commencement of the bolus delivery. For example, either the programming module 60 or infusion pump 22 can be programmed to deliver a bolus of fluid which can automatically prompt the programming module 60, including the occlusion detection program 110, to dynamically adapt such that higher pressure readings in the downstream fluid line do not cause the alarm to be activated. This can allow the bolus to create higher fluid pressure in the downstream fluid line without causing false occlusion alarms.

For example, the programming module 60 and occlusion detection program 110 can dynamically adapt by increasing a maximum allowed pressure to be sensed in the downstream fluid line 31 before activating the alarm. One or more algorithms can be used by either the programming module 60 or occlusion detection program 110 in order to determine appropriate maximum pressures, including pressure ranges, during the delivery of the bolus.

At least some of the increase in pressure during the delivery of a bolus can be due to resistance in the system, such as resistance in the fluid lines. For example, when a bolus is delivered through the downstream fluid line 31, the bolus of fluid acts against resistance in the downstream fluid line 31, such as from the tubing the bolus flows through. In addition, when the bolus acts against the resistance in the system, various characteristics can change and it can take some time for the system to return to a normal state that it was in prior to the delivery of the bolus. For example, the downstream fluid line 31 can expand during delivery of the bolus and it may take some time, measured in seconds to tens of seconds, for the downstream fluid line 31 to relax after the delivery of the bolus. During the period in which the downstream fluid line is relaxing, the infusion rate may return to a programmed infusion rate, such as an infusion rate which was programmed for fluid delivery prior to delivery of the bolus.

In some variations of the system, the programming module can include one or more algorithms which provide a pressure decay rate of the downstream fluid line 31 based on the bolus delivered by the system, when transitioning from a bolus to the primary infusion rate. At least either the programming module or occlusion detection program 110 can use the pressure decay rate to compare to the pressure readings in the downstream fluid line 31 during relaxation of the system after delivery of a bolus in order to prevent the activation of false occlusion alarms. For example, this gradual reduction in expected sensed pressure readings, or pressure decay rate, can consider the time necessary for the fluid lines, such as the downstream fluid line 31, to recover from the delivery of the bolus. Therefore, as the system recovers from the delivery of the bolus, the system gradually lowers the maximum pressure limits, including in conformity with the pressure decay rate, in order to prevent false occlusion alarms, such as from pressure readings outside of an expected pressure range given the programmed infusion rate.

The one or more algorithms which assist in providing the maximum pressures and pressure decay rate can consider a variety of variables when determining the maximum pressures or pressure decay rates. For example, the size and rate of bolus delivery can affect the max pressure and pressure decay rate. The decay rate can include an exponential decay rate. In addition, any number of decay rates can be used for assisting the programming module, including the occlusion detection program, in preventing the false detection of occlusions, particularly during the delivery of a bolus.

An example method of the system includes the programming module 60 being programmed to instruct the infusion pump 22 to deliver a bolus of fluid. The programming module 60 can then automatically and dynamically adapt fluid monitoring features, such as the occlusion detection program 110, in order to prevent false occlusion alarms due to the delivery of the bolus. For example, the bolus information can be input into an algorithm for determining the approximate maximum pressure which can be detected in the downstream fluid line 31, as well as a pressure decay rate for after delivery of the bolus. The programming module 60 and occlusion detection program 110 can use the maximum pressure and pressure decay rate as new pressure limits to compare pressure readings from the downstream pressure sensor 82. Therefore, although at least one spike in pressure may occur during the delivery of the bolus, the occlusion detection program 110 will not activate an alarm unless the pressure reaches beyond the new pressure limits, as defined by the maximum pressure and pressure decay rate, such as due to an actual occlusion in the downstream fluid line.

The one or more pressure sensors, including the downstream pressure sensor 82 and an upstream pressure sensor 80, can take many forms well known to those skilled in the art, including a piezoresistive device. Consequently, no further technical details concerning the mechanical formation of the sensor are presented herein. In addition, at least the downstream pressure can provide pressure signals in response to pressure sensed in the downstream fluid line 31 of the fluid conduit 66. Those pressure signals can be analog in form and can be converted to digital form by an analog-to-digital converter ("A/D") integral with the sensor or by an AID located elsewhere in the data stream.

The processor can be in communication with one or more pumps or pumping mechanisms 70 and it should be understood that other embodiments may exist in which multiple pump channels associated with a multi-channel patient care system may be monitored by the same processor. In such an embodiment, the processor performs the same functions for each pump channel of the system. As an example, FIG. 1 shows a four pump system in which the four pumps 22, 24, 26, and 28 are connected to a common programming module 60 having an internal processor. The processor of the programming module 60 may perform the "infusion rate maintenance" for all four pumps.

System characteristics or other reference values for monitoring fluid flow through the fluid lines, including changes in the fluid line due to the delivery of boluses and the formation of occlusions, can be stored in a memory which can be included in the programming module and which the processor can access. The programs and algorithms of the processor, including the occlusion detection program 110 and algorithms, may be stored in the same memory, or in another memory. Use of memory to store programs and data is well known and no further details are provided here. Values and other programming may also be input into the memory using an input device, such as control keys, or may be preprogrammed.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A patient care system for infusing a medical fluid, the patient care system comprising:
   a fluid supply adapted to hold a medical fluid;

a fluid line providing fluid communication between the fluid supply and a patient;

an infusion pump controlling fluid flow along the fluid line between the fluid container and the patient;

a pressure sensor configured to sense pressure in the fluid line between the infusion pump and the patient; and a programming module including an occlusion detection program and one or more algorithms configured to dynamically adapt, based on a programmed bolus of fluid for delivery to a patient, in order to detect occlusions in the fluid line and prevent activation of a false occlusion alarm, wherein dynamically adapting the programming module includes:

determining that a delivery of a bolus condition has commenced;

increasing a maximum pressure limit that is compared to a sensed pressure of the fluid line between the infusion pump and the patient;

gradually lowering the maximum pressure limit over a predetermined time period after commencement of the delivery of the bolus condition.

2. The patient care system of claim 1, wherein the programming module includes at least one processor and memory.

3. The patient care system of claim 1, wherein a sensed pressure of the fluid line is input into at least one of the occlusion detection program and algorithm.

4. The patient care system of claim 1, wherein the programming module automatically dynamically adapts upon commencing the delivery of the bolus.

5. The patient care system of claim 1, wherein dynamically adapting the programming module includes processing the algorithm having at least information characterizing the programmed bolus and determining at least one of a maximum pressure and a decay rate.

6. The patient care system of claim 5, wherein the decay rate includes an exponential decay rate.

7. The patient care system of claim 5, wherein the occlusion detection program uses at least one of the maximum pressure and decay rate when monitoring the fluid line pressure at least during the delivery of the programmed bolus in order to prevent activation of a false occlusion alarm.

* * * * *